(12) United States Patent
Crisostomo et al.

(10) Patent No.: US 10,195,392 B2
(45) Date of Patent: Feb. 5, 2019

(54) CLIP-ON CATHETER

(71) Applicant: BOSTON SCIENTIFIC SCIMED, INC., Maple Grove, MN (US)

(72) Inventors: Crissly V. Crisostomo, Folsom, CA (US); Randy S. Gamarra, Santa Clara, CA (US); Takashi H. Ino, San Jose, CA (US); Floriza Q. Escalona, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 387 days.

(21) Appl. No.: 15/197,905

(22) Filed: Jun. 30, 2016

(65) Prior Publication Data
US 2017/0000606 A1     Jan. 5, 2017

Related U.S. Application Data

(60) Provisional application No. 62/188,196, filed on Jul. 2, 2015.

(51) Int. Cl.
*A61M 25/00*     (2006.01)
*A61F 2/24*     (2006.01)

(52) U.S. Cl.
CPC ....... *A61M 25/0009* (2013.01); *A61F 2/2436* (2013.01); *A61M 25/0012* (2013.01); *A61M 25/0013* (2013.01); *A61M 25/0026* (2013.01)

(58) Field of Classification Search
CPC ............ A61M 25/0026; A61M 25/007; A61M 2025/1093; A61M 25/0068;
(Continued)

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| CN | 1338951 A | 3/2002 |
|---|---|---|
| DE | 19532846 A1 | 3/1997 |

(Continued)

OTHER PUBLICATIONS

Andersen et al., "Transluminal implantation of artificial heart valves. Description of a new expandable aortic valve and initial results with implantation by catheter technique in closed chest pigs." Euro. Heart J., 13:704-708, May 1992.

(Continued)

*Primary Examiner* — Katrina Stransky
*Assistant Examiner* — Michael Mendoza
(74) *Attorney, Agent, or Firm* — Seager, Tufte & Wickhem LLP.

(57) ABSTRACT

A medical device may include a device handle having a diverter block non-movably disposed within an interior cavity of the handle, the diverter block including at least one lumen extending longitudinally therethrough and a distal mounting portion. A delivery sheath may be coupled to the device handle. A catheter assembly may extend distally from the device handle within the delivery sheath. The catheter assembly may include a multi-lumen polymeric shaft coupled to the diverter block, and a metallic hypotube section disposed about and fixedly attached to a proximal end of the shaft. The hypotube section may releasably lock the shaft to the diverter block in fluid communication with the at least one lumen of the diverter block. The delivery sheath may be axially translatable relative to the device handle and the catheter assembly may be fixed in position relative to the device handle.

19 Claims, 10 Drawing Sheets

(58) Field of Classification Search
CPC .......... A61M 25/0074; A61M 25/1025; A61M 2025/0681; A61M 25/0069; A61M 25/00; A61M 39/10
USPC ................................ 604/533, 535, 536, 319
See application file for complete search history.

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Komberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |

(56) References Cited

U.S. PATENT DOCUMENTS

| | | |
|---|---|---|
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |

(56) References Cited

U.S. PATENT DOCUMENTS

| | | |
|---|---|---|
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |

(56) References Cited

U.S. PATENT DOCUMENTS

| | | |
|---|---|---|
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |

(56) References Cited

U.S. PATENT DOCUMENTS

| | | |
|---|---|---|
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |

(56) References Cited

U.S. PATENT DOCUMENTS

| | | |
|---|---|---|
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |

(56) References Cited

FOREIGN PATENT DOCUMENTS

| | | | |
|---|---|---|---|
| WO | 2005002466 A2 | 1/2005 | |
| WO | 2005004753 A1 | 1/2005 | |
| WO | 2005009285 A2 | 2/2005 | |
| WO | 2005011534 A1 | 2/2005 | |
| WO | 2005011535 A2 | 2/2005 | |
| WO | 2005023155 A1 | 3/2005 | |
| WO | 2005027790 A1 | 3/2005 | |
| WO | 2005046528 A1 | 5/2005 | |
| WO | 2005046529 A1 | 5/2005 | |
| WO | 2005048883 A1 | 6/2005 | |
| WO | 2005062980 A2 | 7/2005 | |
| WO | 2005065585 A1 | 7/2005 | |
| WO | 2005084595 A1 | 9/2005 | |
| WO | 2005087140 A1 | 9/2005 | |
| WO | 2005096993 A1 | 10/2005 | |
| WO | 2006005015 A2 | 1/2006 | |
| WO | 2006009690 A1 | 1/2006 | |
| WO | 2006027499 A2 | 3/2006 | |
| WO | 2006138391 A2 | 12/2006 | |
| WO | 2007033093 A2 | 3/2007 | |
| WO | 2007035471 A2 | 3/2007 | |
| WO | 2007044285 A2 | 4/2007 | |
| WO | 2007053243 A2 | 5/2007 | |
| WO | 2007058847 A2 | 5/2007 | |
| WO | 2007092354 A2 | 8/2007 | |
| WO | 2007097983 A2 | 8/2007 | |
| WO | 2010042950 A2 | 4/2010 | |
| WO | 2012116368 A2 | 8/2012 | |

OTHER PUBLICATIONS

Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses" Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcitic Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.

Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. 9-17, Feb. 2004.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
Examiner's First Report on AU Patent Application No. 2011202667, dated May 17, 2012.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Atwood et al., "Insertion of Heart Valves by Catheterization." The Capstone Design Course Report. MIME 1501-1502. Technical Design Report. Northeastern University, pp. 1-93, Nov. 5, 2007.
Supplemental Search Report from EP Patent Office, EP Application No. 04813777.2, dated Aug. 19, 2011.
Supplemental Search Report from EP Patent Office, EP Application No. 04815634.3, dated Aug. 19, 2011.
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report for EP Application No. 06824992.9, dated Aug. 10, 2011.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, Feb. 2006.
Levy, "Mycobacterium Chelonei Infection of Porcine Heart Valves." The New England Journal of Medicine, Washington DC, 297(12), Sep. 22, 1977.
Supplemental Search Report from EP Patent Office, EP Application No. 05758878.2, Oct. 24, 2011.

(56) References Cited

OTHER PUBLICATIONS

"Pericardial Heart Valves." Edwards Lifesciences, Cardiovascular Surgery FAQ, http://www.edwards.com/products/cardiovascularsurgeryfaq.htm, Nov. 14, 2010.

Southern Lights Biomaterials Homepage, http://www.slv.co.nz/, Jan. 7, 2011.

Stassano. "Mid-term Results of the Valve-on-Valve Technique for Bioprosthetic Failure." European Journal of Cardiothoracic Surgery: vol. 18, 453-457, Oct. 2000.

Topol. "Percutaneous Expandable Prosthetic Valves." Textbook of Interventional Cardiology, W.B. Saunders Company, 2: 1268-1276, 1994.

CLIP-ON CATHETER

RELATED APPLICATIONS

This application claims the benefit of U.S. Provisional Application No. 62/188,196, filed Jul. 2, 2015.

TECHNICAL FIELD

The present disclosure pertains to medical devices, and methods for manufacturing medical devices. More particularly, the present disclosure pertains to medical devices for a replacement heart valve and methods for manufacturing medical devices for use with a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a catheter assembly may comprise an elongate polymeric shaft having a plurality of lumens extending therethrough, and a metallic hypotube section disposed about and fixedly attached to a proximal end of the polymeric shaft. The metallic hypotube section may include a plurality of apertures extending through a wall thereof and a plurality of cutouts each defining a corresponding prong. Each prong may extend radially outward from the wall.

In addition or alternatively, and in a second aspect, each prong extends radially outward at an oblique angle to the wall.

In addition or alternatively, and in a third aspect, the metallic hypotube section includes a smooth portion on its outer surface proximal of the plurality of cutouts.

In addition or alternatively, and in a fourth aspect, the smooth portion extends uninterruptedly around the metallic hypotube section to form an annular ring.

In addition or alternatively, and in a fifth aspect, at least some of the plurality of apertures are disposed proximal of the smooth portion.

In addition or alternatively, and in a sixth aspect, at least some of the plurality of apertures are disposed distal of the plurality of cutouts.

In addition or alternatively, and in a seventh aspect, a catheter assembly may further comprise at least one piece of polymeric material disposed about the metallic hypotube section and extending through the plurality of apertures to mechanically fix the metallic hypotube section to the polymeric shaft.

In addition or alternatively, and in an eighth aspect, a medical device may comprise a device handle having a diverter block non-movably disposed within an interior cavity of the device handle, the diverter block including at least one lumen extending longitudinally therethrough and a distal mounting portion in fluid communication with the at least one lumen, a delivery sheath coupled to the device handle, and a catheter assembly extending distally from the device handle within the delivery sheath. The catheter assembly may comprise a multi-lumen polymeric shaft coupled to the diverter block, and a metallic hypotube section disposed about and fixedly attached to a proximal end of the polymeric shaft. The metallic hypotube section may releasably lock the polymeric shaft to the diverter block in fluid communication with the at least one lumen of the diverter block. The delivery sheath may be axially translatable relative to the device handle and the catheter assembly is fixed in position relative to the device handle.

In addition or alternatively, and in a ninth aspect, the metallic hypotube section includes a plurality of apertures extending through a wall thereof and a plurality of cutouts each defining a corresponding prong extending radially outward from the wall.

In addition or alternatively, and in a tenth aspect, the distal mounting portion of the diverter block includes a plurality of windows formed therein, and each prong engages one of the plurality of windows.

In addition or alternatively, and in an eleventh aspect, each prong extends radially outward at an oblique angle to the wall.

In addition or alternatively, and in a twelfth aspect, the metallic hypotube section includes a smooth portion on its outer surface proximal of the plurality of cutouts.

In addition or alternatively, and in a thirteenth aspect, a medical device may further include a gasket compressed between the smooth portion of the metallic hypotube section and the distal mounting portion of the diverter block.

In addition or alternatively, and in a fourteenth aspect, the gasket is disposed within a channel formed in the distal mounting portion.

In addition or alternatively, and in a fifteenth aspect, the catheter assembly further comprises at least one piece of polymeric material disposed about the metallic hypotube section and extending through the plurality of apertures to mechanically fix the metallic hypotube section to the polymeric shaft.

In addition or alternatively, and in a sixteenth aspect, a method of manufacturing a catheter assembly may comprise forming a polymeric shaft having a plurality of lumens extending therethrough, cutting a plurality of apertures through a wall of a hypotube section, cutting a plurality of cutouts in the wall of the hypotube section to define a prong within each cutout, angling the prongs radially outward from the wall of the hypotube section, inserting a proximal end of the polymeric shaft within the hypotube section, applying polymeric material onto the hypotube section over the plurality of apertures, and applying heat to the catheter assembly to reflow the polymeric material through the plurality of apertures and bond with the polymeric shaft, thereby mechanically fixing the hypotube section to the polymeric shaft.

In addition or alternatively, and in a seventeenth aspect, the plurality of cutouts is cut using a laser.

In addition or alternatively, and in an eighteenth aspect, the plurality of apertures is cut using a laser.

In addition or alternatively, and in a nineteenth aspect, the prongs are angled radially outward at an oblique angle to the wall of the hypotube section.

In addition or alternatively, and in a twentieth aspect, the plurality of apertures includes a first plurality of apertures and a second plurality of apertures, the first plurality of apertures being disposed proximal of the plurality of cutouts and the second plurality of apertures being disposed distal of the plurality of cutouts. The hypotube section includes a smooth portion configured to engage a gasket surrounding the hypotube section, the smooth portion being disposed between the plurality of cutouts and the first plurality of apertures.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
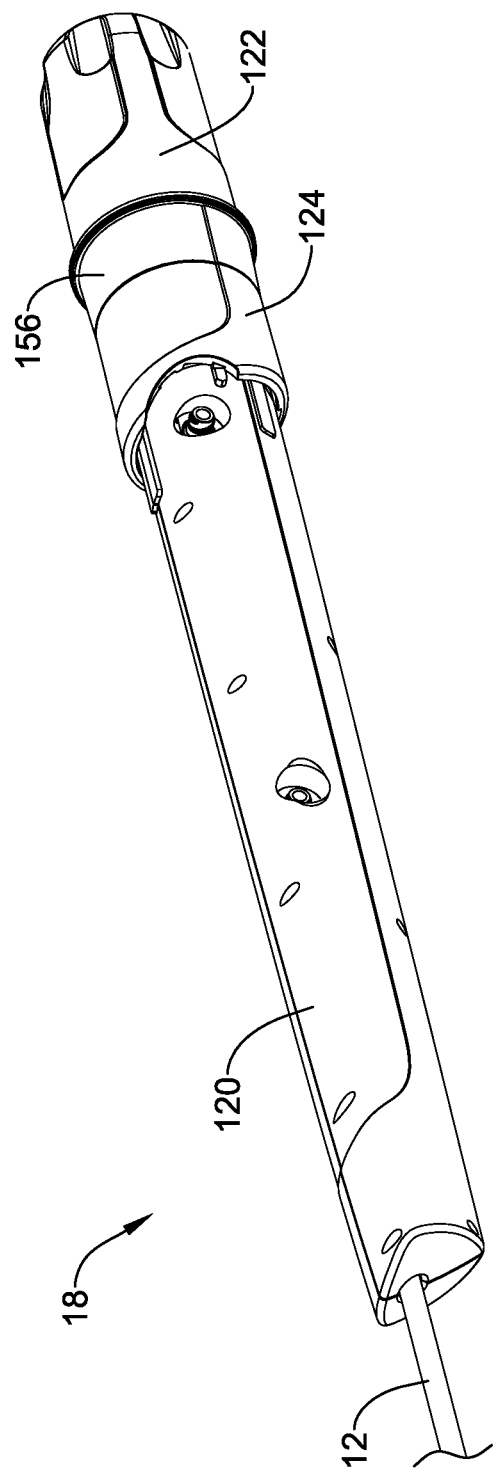
FIG. 1 illustrates of a portion of example medical device system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a perspective view of a portion of an example medical device system 10. It should be noted that some features of medical device system 10 are not shown, or are shown schematically, in the figures for simplicity. Additional details regarding some of the aspects of the medical device system 10 are provided in other figures in greater detail. A medical device system 10 may be used to deliver and/or deploy a variety of medical devices to a number of locations within the anatomy. In at least some embodiments, the medical device system 10 is a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

Figure 2:
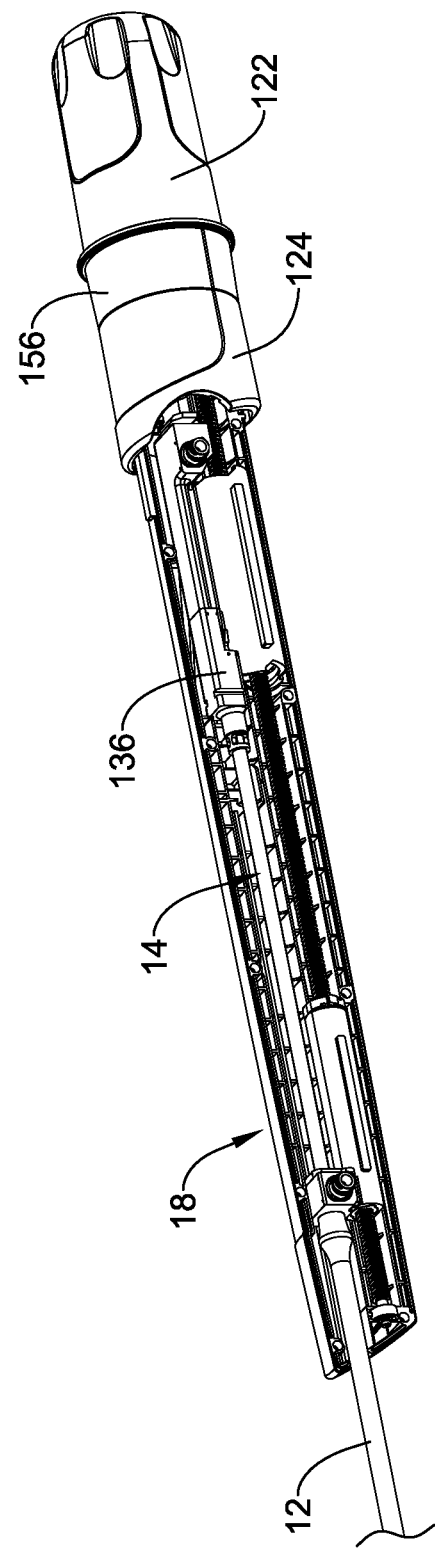
FIG. 2 is a partial cut-away view of an example medical device system.

The medical device system 10 may generally be described as a catheter system that includes a delivery sheath 12 coupled to a device handle 18, and a catheter assembly 14 (not shown in FIG. 1) extending distally from the device handle 18 within the delivery sheath 12, as may be seen in the partial cut-away view of FIG. 2. A medical device implant (not shown) may be coupled to the catheter assembly 14 and disposed within the delivery sheath 12 during delivery of the medical device implant. The device handle 18 may generally be disposed at a proximal end of the delivery sheath 12 and/or the catheter assembly 14. In at least some embodiments, the medical device implant may be disposed at, attached at, coupled to, received within, and/or disposed within a distal end of the delivery sheath 12 and/or distal of the catheter assembly 14. In some embodiments, the delivery sheath 12 may be axially translatable relative to the device handle 18 and/or the catheter assembly 14. In some embodiments, the catheter assembly 14 may be fixedly attached to and/or fixed in position relative to the device handle 18. In general, the device handle 18 may be configured to manipulate the position of the delivery sheath 12 relative to the catheter assembly 14 as well as aid in the deployment of the medical device implant.

In use, the medical device system 10 may be advanced percutaneously through a patient's vasculature to a position adjacent to an area of interest. For example, the medical device system 10 may be advanced through the patient's vasculature to a position adjacent to a defective aortic valve. During delivery, the medical device implant may be generally disposed in an elongated and low profile "delivery" configuration at, coupled to, and/or within the delivery sheath 12 distally of the catheter assembly 14. Once positioned, the device handle 18 may be actuated to proximally retract the delivery sheath 12 relative to the catheter assembly 14, which may be held stationary by the device handle 18, to expose the medical device implant. The medical device implant may be actuated in order to expand the medical device implant into a generally shortened and larger profile "deployed" configuration suitable for implantation within the anatomy. When the medical device implant is suitably deployed within the anatomy, the medical device implant may be released and/or detached from the medical device system 10, and the medical device system 10 can be removed from the vasculature, leaving the medical device implant in place to function as, for example, a suitable replacement for a native aortic valve. In at least some interventions, the medical device implant may be deployed within the native aortic valve (e.g., the native valve is left in place and not excised). Alternatively, the native aortic valve may be removed (such as through valvuloplasty, for example) and the medical device implant may be deployed in its place as a replacement.

In some embodiments, the delivery sheath 12 may define a proximal portion and a distal portion. In some embodiments, the distal portion may have a slightly enlarged or flared inner diameter, which may provide additional space for holding the medical device implant therein. In some embodiments, an inner diameter of the delivery sheath 12 along the proximal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388±0.0508 cm (0.222±0.002 inches). In some embodiments, an inner diameter of the delivery sheath 12 along the distal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). In some embodiments, at the distal end of the distal portion may be a distal tip, which may be flared or otherwise have a funnel-like shape. The funnel-like shape may increase the outer diameter (and the inner diameter) of the delivery sheath 12 at the distal tip and in some embodiments may aid in the sheathing and/or re-sheathing of the medical device implant into the delivery sheath 12. In some embodiments, other than at the distal tip, the delivery sheath 12 may have a generally constant outer diameter. For example, the delivery sheath 12 may have an outer diameter in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including children) and/or arrangements for the outer diameter and/or the inner diameter of the delivery sheath 12. These contemplated embodiments include delivery sheaths with flared or otherwise variable outer diameters, embodiments with constant inner diameters, combinations thereof, and the like. In some embodiments, the delivery sheath 12 may also have a length that is appropriate for reaching the intended area of interest within the anatomy. For example, in some embodiments, the delivery sheath 12 may have a length in the range of about 30 to 200 cm, or about 60 to 150 cm, or about 100 to 120 cm, or about 108±0.20 cm. In some embodiments, the delivery sheath 12 and/or one or more portions of the delivery sheath 12 may be curved. For example, in some embodiments, the distal portion of the delivery sheath 12 may be curved. In one example, a radius of the curved distal portion (as measured from a central axis of the delivery sheath 12) may be in the range of about 2 to 6 cm (20 to 60 mm), or about 3 to 4 cm (30 to 40 mm), or about 3.675 cm (36.75 mm). Again, these dimensions are examples and are not intended to be limiting.

In some embodiments, a delivery sheath 12 may be formed from a singular monolithic tube or unitary member. Alternatively, the delivery sheath 12 may include a plurality of layers or portions. One or more of these layers may include a reinforcing structure such as a braid, coil, mesh, combinations thereof, or the like. For example, in some embodiments, the delivery sheath 12 may include an inner liner or layer. In some embodiments, an intermediate or tier layer may be disposed on the inner liner. In some embodiments, a reinforcement may be disposed on the intermediate layer. In some embodiments, a topcoat or outer layer may be disposed on or over the reinforcement. In some embodiments, an outer coating (e.g., a lubricious coating, a hydrophilic coating, a hydrophobic coating, etc.) may be disposed on, over, and/or along portions or all of the topcoat or outer layer. These are just examples. Several alternative structural configurations are contemplated for the delivery sheath 12 including embodiments including two or more layers that may be different, embodiments without a reinforcement, and the like, or other suitable configurations.

The dimensions and materials utilized for the various layers of the delivery sheath 12 may also vary. For example, an inner liner may include a polymeric material such as fluorinated ethylene propylene (FEP) and may have a thickness in the range of about 0.00254 to 0.0127 cm (0.001 to 0.005 inches) or about 0.00762±0.00254 (0.003±0.001 inches), an intermediate layer may include a polymer material such as polyether block amide (e.g., PEBAX 6333) and may have a thickness in the range of about 0.00254 to 0.0127 cm (0.001 to 0.005 inches) or about 0.00508±0.00254 (0.002±0.001 inches), an outer coating may include a polymer material such as polyether block amide (e.g., PEBAX 7233) and may have a thickness in the range of about 0.00254 to 0.0254 cm (0.001 to 0.01 inches). In some embodiments, an outer coating may vary in thickness. For example, along a proximal portion, an outer coating may have greater thickness, such as about 0.0127 to about 0.0508 cm or about 0.02159 cm (0.005 to 0.02 inches or about 0.0085 inches), than along a distal portion and/or at a distal tip, which may be about 0.0127 to about 0.0508 cm or about 0.01651 cm (e.g., about 0.005 to 0.02 inches or about 0.0065 inches). These are just examples as other suitable materials may be used.

A reinforcement may also vary in form. In at least some embodiments, a reinforcement may take the form of a braid, coil, mesh, or the like. For example, in some embodiments, a reinforcement may include a metallic braid (e.g., stainless steel). In some of these embodiments, a reinforcement may also include additional structures such as one or more longitudinally-extending strands. For example, a reinforcement may include a pair of longitudinally-extending aramid and/or para aramid strands (for example, KEVLAR®) disposed on opposite sides of the braid. In some embodiments, these strands may or may not be woven into portions or all of the braid.

In some embodiments, a distal end region of the catheter assembly 14 may include a step in outer diameter that defines a decreased outer diameter section. For example, a decreased outer diameter section may have an outer diameter in the range of about 0.127 to 0.635 cm (0.05 to 0.25 inches), or about 0.254 to 0.508 cm (0.10 to 0.20 inches), or about 0.38608±0.00762 (0.152±0.003 inches) as opposed to the remainder of the catheter assembly 14 where the outer diameter may be in the range of about 0.127 to 0.762 cm (0.05 to 0.30 inches), or about 0.254 to 0.635 cm (0.10 to 0.25 inches), or about 0.508±0.0254 cm (0.20±0.01 inches). The decreased outer diameter section may define a region where other components of the medical device system 10 may be attached.

In some embodiments, the catheter assembly 14 may include an extruded, multi-lumen polymeric shaft 20. Other forms are also contemplated including other polymer shafts or tubes, metallic shafts or tubes, reinforced shafts or tubes, or the like including other suitable materials such as those disclosed herein. In some embodiments, the polymeric shaft 20 may be a singular monolithic or unitary member. In some embodiments, the polymeric shaft 20 may include a plurality of portions or segments that are coupled together. The total length of the catheter assembly 14 and/or the polymeric shaft 20 may be in the range of about 60 to 150 cm, or about 80 to 120 cm, or about 100 to 115 cm, or about 112±0.02 cm. Just like the delivery sheath 12, in some embodiments, the catheter assembly 14 and/or the polymeric shaft 20 may be curved, for example adjacent to a distal end thereof. In some embodiments, the polymeric shaft 20 may have one or more sections with a differing hardness/stiffness (e.g., differing shore durometer). For example, the polymeric shaft 20 may have a proximal region and an intermediate region. In some embodiments, the proximal region may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. In some embodiments, the intermediate region may include a 40D polyether block amide (e.g., 40D PEBAX) and may have a length in the range of about 5 to 25 mm, or about 10 to 20 mm, or about 15±0.01 mm. The decreased outer diameter section may also differ from the proximal region and/or the intermediate region and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

In some embodiments, the polymeric shaft 20 may include one or more lumens extending at least partially therethrough. For example, FIG. 3 (which is a perspective view of a portion of the catheter assembly 14) illustrates that, in some embodiments, the polymeric shaft may include a first lumen, a second lumen, a third lumen, and/or a fourth lumen. In general, the lumens extend along the entire length of the catheter assembly 14 and/or the polymeric shaft 20. Other embodiments are contemplated, however, where one or more of lumens extend along only a portion of the length of catheter assembly 14 and/or the polymeric shaft 20. For example, the fourth lumen may stop just short of the distal end of the catheter assembly 14 and/or the polymeric shaft 20 and/or be filled in at its distal end to effectively end the fourth lumen proximal of the distal end of the catheter assembly 14 and/or the polymeric shaft 20.

Disposed within one of the lumens (e.g., a first lumen) may be one or more push-pull rods, which are used to expand and/or elongate the medical device implant when the device handle 18 is actuated by connecting a portion of the device handle 18 to the medical device implant to transmit rotational and/or axial motion thereto. In some embodiments, one or more of the lumens (e.g., the first lumen) may be lined with a low friction liner (e.g., a FEP liner). Disposed within a second lumen may be a pin release mandrel, which in some embodiments may facilitate release of the medical device implant. In some embodiments, the second lumen may be lined with a hypotube liner. In some embodiments, a third lumen may be a guidewire lumen. In some embodiments, the third lumen may be lined with a hypotube liner. In some embodiments, a fourth lumen may be used to house a non-stretch wire or member. The form of the non-stretch wire or member may vary. In some embodiments, the non-stretch wire or member may take the form of a stainless steel braid. The non-stretch wire or member may optionally include a pair of longitudinally-extending aramid and/or para aramid strands (for example, KEVLAR®) disposed on opposite sides of the braid. In general, rather than being "disposed within" the fourth lumen, the non-stretch wire or member may be embedded within the fourth lumen and/or the polymeric shaft 20. In addition, the non-stretch wire or member may extend to a position adjacent to the distal end portion but not fully to the distal end of the catheter assembly 14 and/or the polymeric shaft 20. For example, a short distal segment of the fourth lumen may be filled in with polymer material adjacent to the distal end of catheter assembly 14 and/or the polymeric shaft 20.

The catheter assembly 14 may also include a guidewire extension tube (not shown) that extends distally from the distal end thereof. A nose cone (not shown) may be attached to the guidewire extension tube. The nose cone generally may be designed to have an atraumatic shape. The nose cone may also include a ridge or ledge that is configured to abut the distal end or distal tip of the delivery sheath 12 during delivery of the medical device implant.

As can be seen in FIGS. 1 and 2, the device handle 18 includes a handle housing 120. In some embodiments, the device handle 18 may also include a rotatable control knob 122 disposed on or about the handle housing 120 (e.g., at a proximal end of the handle housing 120) and may be used to move one or more of the components of the medical device system 10 (e.g., the delivery sheath 12, the push-pull rods, the pin release mandrel, etc.). In some embodiments, the device handle 18 may include a rotatable collar 156 disposed about the handle housing 120. In some embodiments, the rotatable collar 156 may be disposed adjacent the rotatable control knob 122. In some embodiments, the rotatable control knob 122 may be disposed about a proximal portion of the rotatable collar 156. In some embodiments, a slidable door 124 may also be disposed about the handle housing 120. In some embodiments, the slidable door 124 may translate distally to expose a distal portion of the rotatable collar 156 which may be positioned generally under the slidable door 124. In some embodiments, the rotatable collar 156 may be rotated to move one or more components of the medical device system 10. In some embodiments, the device handle 18 may also include one or more apertures and/or flush ports that can be used to flush the medical device system 10. In some embodiments, a distal flush port and a proximal flush port may be accessible from an exterior of the handle housing 120 through a distal aperture and a proximal aperture, respectively.

FIG. 2 is a perspective view of the device handle 18 with a portion of the handle housing 120 removed, exposing at least some of the interior components. Here it can be seen that the delivery sheath 12 may be fixedly attached to a sheath adapter. The sheath adapter may be attached to a sheath carriage, which may be threaded onto a lead screw. The distal flush port may be disposed on the sheath adapter. In general, the distal flush port provides access to the interior or lumen of the delivery sheath 12 (e.g., access to space between the catheter assembly 14 and the delivery sheath 12) so that a clinician can flush fluid through the lumen of the delivery sheath 12 to remove any unwanted materials (e.g., air, fluid, contaminants, etc.) therein prior to use of the medical device system 10. In at least some embodiments, the distal flush port has a luer type connector (e.g., a one-way luer connector) that allows a device such as a syringe with a corresponding connector to be attached thereto for flushing.

Extending through and proximally from the sheath adapter is the catheter assembly 14. A proximal end of the catheter assembly 14 is selectively attached (e.g., releasably locked) to a diverter block 136. The diverter block 136 may be attached to a support body. The proximal flush port may be disposed on the support body and can be used to flush the lumen(s) of the catheter assembly 14 and/or the polymeric shaft 20, and may function similarly to the distal flush port, for example. In general, the diverter block 136 and/or the support body may have one or more passageways or lumens formed therein.

In some embodiments, the push-pull rods and/or the pin release mandrel may extend from a mechanism operatively connected to the rotatable control knob 122, the slidable door 124, and/or the rotatable collar 156 through respective passageways or lumens in the diverter block 136 and/or the support body and into the lumen(s) of the catheter assembly 14 and/or the polymeric shaft 20. Alternatively, the proximal ends of the push-pull rods and/or the pin release mandrel may each be attached to a shaft or hypotube (e.g., solid in cross-section, tubular, etc.), and each of the shafts or hypotubes may extend proximally therefrom through one of the one or more passageways or lumens to the mechanism operatively connected to the rotatable control knob 122, the slidable door 124, and/or the rotatable collar 156. For example, a first shaft or hypotube and a second shaft or hypotube may extend through the passageways or lumens in the diverter block 136, and in some embodiments, the first shaft or hypotube may extend through a first passageway or lumen and the second shaft or hypotube may extend through a second passageway or lumen that is separate or distinct from the first passageway or lumen. In at least some embodiments, the first shaft may be attached to the pin release mandrel. In at least some embodiments, the second shaft may be attached to the push-pull rods. It should be noted that at in least some embodiments of the medical device system 10, three push-pull rods are utilized. In these embodiments, the three push-pull rods may come together (e.g., brought into contact with one another or otherwise brought into relatively close proximity with one another) adjacent to the distal end of the catheter assembly 14 and enter the first passageway or lumen. At one or more positions along their length, the push-pull rods may be fixedly attached to one another. For example, in some embodiments, the push-pull rods may be welded together about 10.16 cm (about 4.00 inches) proximally from their distal ends. In some embodiments, the push-pull rods may be welded together proximate their proximal ends in addition to or instead of the distal weld. Proximally thereafter, the push-pull rods may extend to the second shaft.

In some embodiments, a hypotube (e.g., a hypotube liner disposed along a guidewire lumen) may extend through the diverter block 136 within a passageway or lumen therein and then be "diverted" around a portion of the diverter block 136 and/or the support body, and ultimately be extended to a position at the proximal end of the device handle 18 so as to provide a user access to the guidewire lumen.

The device handle 18 is generally configured for coordinated movement of multiple structures of the medical device system 10. For example, the device handle 18 is configured to allow a user to move the delivery sheath 12 (e.g., relative to the catheter assembly 14), move the push-pull rods, and move the pin release mandrel. Moreover, the device handle 18 is configured so that the appropriate structure can be moved at the appropriate time during the intervention so that the medical device implant can be delivered in an efficient manner.

To help facilitate the coordinated movement, the device handle 18 may include one or more mechanisms disposed therein which may translate, transfer, and/or convert motion (e.g., rotational motion) of the rotatable control knob 122, the slidable door 124, and/or the rotatable collar 156 into axial motion, movement, and/or translation at a distal end of the medical device system 10.

To help facilitate the coordinated movement, the device handle 18 may include a lost motion barrel. The lost motion barrel may be configured to engage carriages and/or screws associated with the carriages at different times during the intervention to stop motion (e.g., create "lost motion" of the appropriate carriage). Upon rotation of the rotatable control knob 122 (e.g., in the clockwise direction), the lead screw begins to rotate. Rotation of the lead screw causes the sheath carriage to move along the lead screw in the proximal direction, resulting in proximal movement of the delivery sheath 12 relative to the catheter assembly 14 and/or the device handle 18 (e.g., "unsheathing" the medical device implant).

Eventually, sufficient actuation of the rotatable control knob 122, the slidable door 124, and/or the rotatable collar 156, and the operatively connected mechanism(s) of the device handle 18, may actuate the medical device implant from the delivery configuration to the deployed configuration, and may further release and/or detach the medical device implant from the catheter assembly 14 and/or the medical device system 10.

Figure 3:
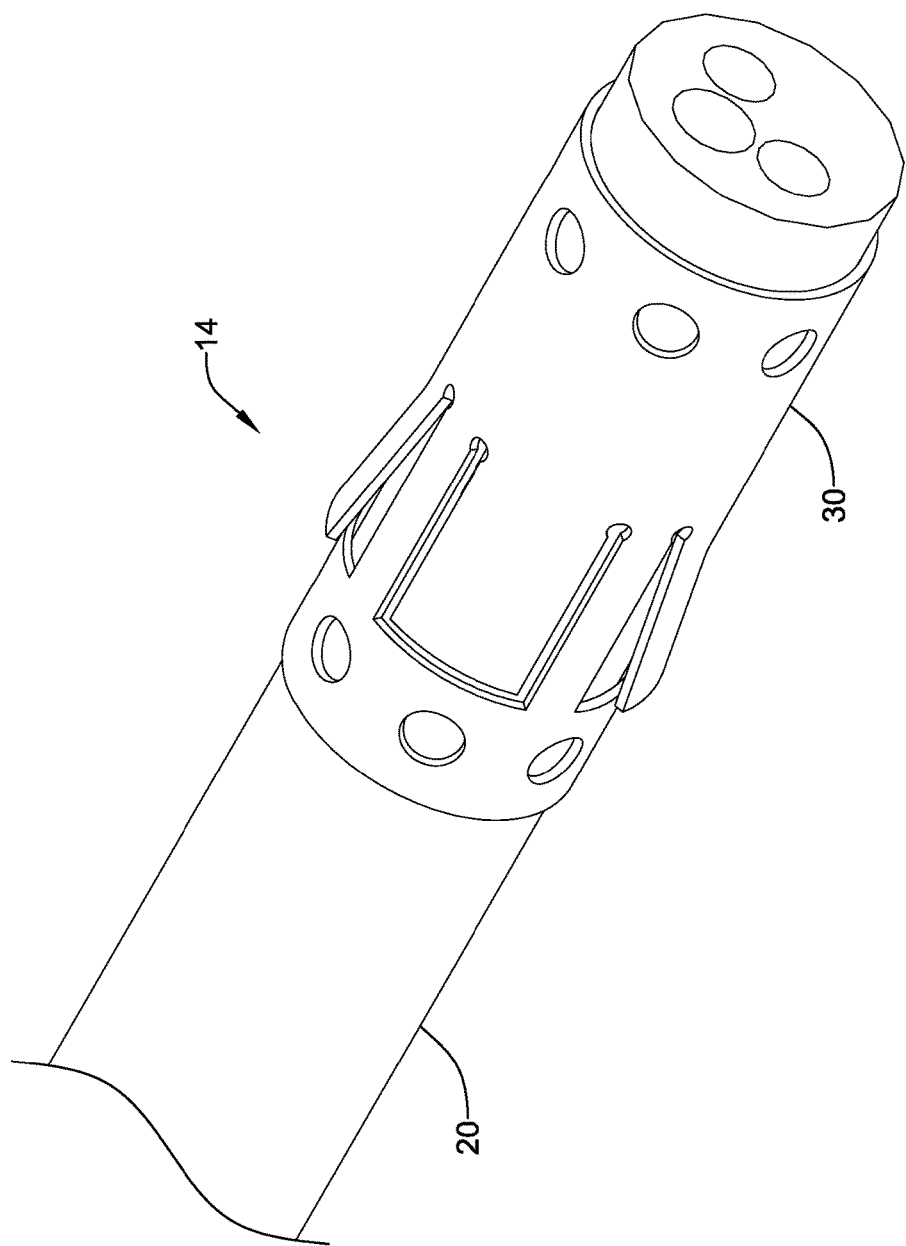
FIG. 3 is perspective view of a portion of example catheter assembly.

FIG. 3 is a perspective view of a proximal portion of the catheter assembly 14. In some embodiments, the catheter assembly 14 may include an elongate polymeric shaft 20 having a plurality of lumens extending therethrough. In some embodiments, the elongate polymeric shaft 20 may include one lumen, two lumens, three lumens, four lumens, five lumens, or another suitable quantity of lumens extending therethrough. In some embodiments, the catheter assembly 14 may include a metallic hypotube section 30 disposed about the polymeric shaft 20. In some embodiments, the metallic hypotube section 30 may be slidable and/or rotatable on the polymeric shaft 20. In some embodiments, the metallic hypotube section 30 may form an interference fit with the polymeric shaft 20. In some embodiments, the metallic hypotube section 30 may be assembled onto the polymeric shaft 20 and then attached to, coupled with, bonded to, or otherwise fixed to the polymeric shaft 20. In some embodiments, the catheter assembly 14 may include a metallic hypotube section 30 fixedly attached to a proximal end of the polymeric shaft 20. For example, in some embodiments, the metallic hypotube section 30 may be press-fit onto the polymeric shaft 20, adhesively bonded to the polymeric shaft 20, and/or mechanically fixed to the polymeric shaft 20.

Figure 4:
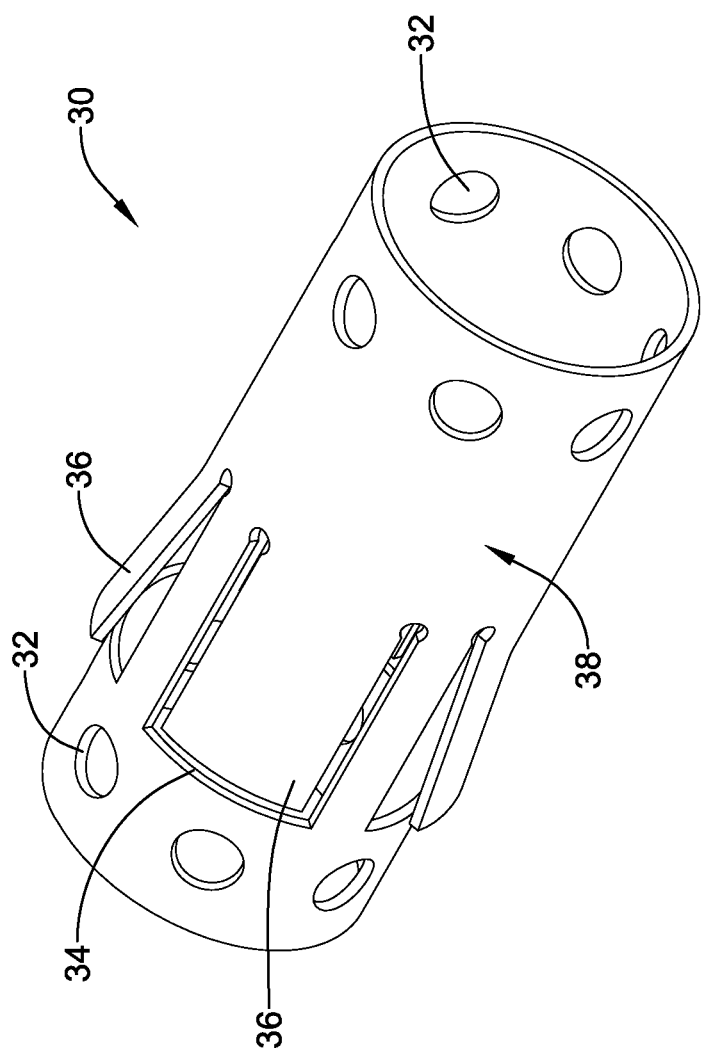
FIG. 4 is a perspective view of an example hypotube section.

As may be seen in FIG. 4, for example, a metallic hypotube section 30 may include a plurality of apertures 32 extending through a side wall of the metallic hypotube section 30. In some embodiments, the metallic hypotube section 30 may include a plurality of cutouts 34 formed through the side wall of the metallic hypotube section 30, each defining a corresponding prong 36. In some embodiments, one or more of the prongs 36 may extend radially outward from the side wall of the metallic hypotube section 30 in a distal direction. In some embodiments, each prong 36 may extend radially outward from the side wall of the metallic hypotube section 30 in the distal direction. In some embodiments, each prong 36 may extend radially outward from the side wall of the metallic hypotube section 30 at an oblique angle relative to the side wall of the metallic hypotube section 30 to form an angled-out configuration in the distal direction. In some embodiments, each prong 36 may be self-biased toward the angled-out configuration, wherein the prong(s) 36 may be deflected inward by sufficient inward pressure applied to an outer surface of the prong(s) 36, and each prong 36 is configured to rebound toward and/or to the angled-out configured upon reduction and/or removal of the inward pressure applied to the outer surface of the prong(s) 36. Such a construction may permit a lockable connection between the catheter assembly 14 and a diverter block 136 with a snap-fit connection, as described herein.

In some embodiments, the metallic hypotube section 30 may include a smooth portion 38 on its outer surface proximal of the plurality of cutouts 34. In some embodiments, the smooth portion 38 may extending uninterruptedly and/or circumferentially around the metallic hypotube section 30 to form an annular ring. In some embodiments, the smooth portion 38 may extend intermittently and/or discontinuously around the metallic hypotube section 30. In some embodiments, at least some of the plurality of apertures 32 may be disposed proximal of the smooth portion 38. In some embodiments, at least some of the plurality of apertures 32 may be disposed distal of the plurality of cutouts 34 and/or the corresponding prongs 36, which may be angled radially outward in the distal direction. In some embodiments, the plurality of apertures 32 may extend circumferentially around the metallic hypotube section 30. In some embodiments, the plurality of apertures 32 may be disposed at regular intervals (e.g., angles, circumferential distance, arc length, etc.) about a central longitudinal axis of the metallic hypotube section 30. In some embodiments, the plurality of apertures 32 may be disposed at irregular intervals (e.g., angles, circumferential distance, arc length, etc.) about a central longitudinal axis of the metallic hypotube section 30.

Figure 5:
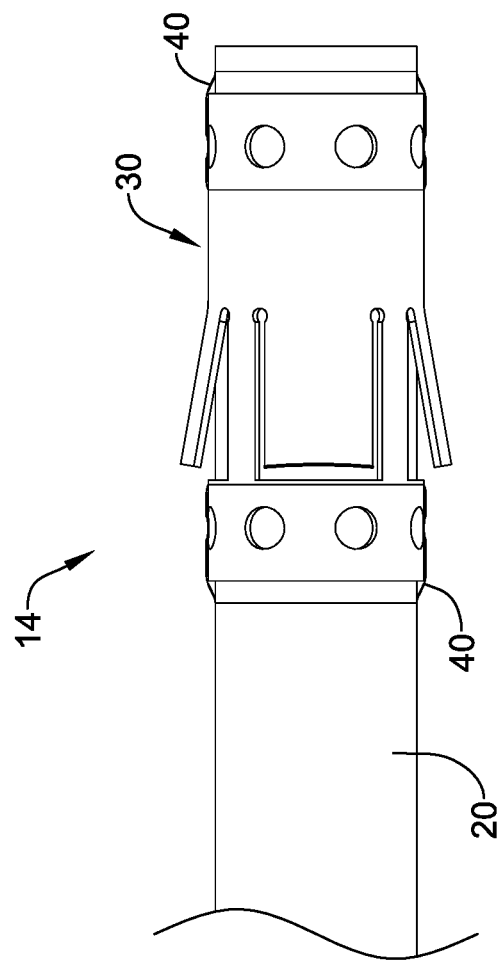
FIG. 5 is a side view of a portion of example catheter assembly.

In some embodiments, the metallic hypotube section 30 may be fixedly attached to a proximal portion of the polymeric shaft 20, as discussed above, with the prong(s) 36 angled radially outward in the distal direction. In some embodiments, at least one piece of polymeric material 40 may be disposed about the metallic hypotube section 30 and the polymeric shaft 20. In some embodiments, the at least one piece of polymeric material 40 may overlap a portion of the metallic hypotube section 30 and a portion of the polymeric shaft 20. In some embodiments, the at least one piece of polymeric material 40 may overlap at least a portion of the plurality of apertures 32 of the metallic hypotube section 30. In some embodiments, the at least one piece of polymeric material 40 may completely overlap the plurality of apertures 32 of the metallic hypotube section 30. In some embodiments, the at least one piece of polymeric material 40 may completely encircle and/or surround the polymeric shaft 20. During manufacturing of the catheter assembly 14, as described in more detail below, the catheter assembly 14 (including the polymeric shaft 20, the metallic hypotube section 30, and the at least one piece of polymeric material 40) may be heated to a temperature sufficient to at least partially melt the polymeric material 40 and/or the polymeric shaft 20. In doing so, the at least one piece of polymeric material 40 overlapping the plurality of apertures 32 may melt and flow into the plurality of apertures 32 and into contact with the polymeric shaft 20. In some embodiments, after heating, the at least one piece of polymeric material 40 may extend through the plurality of apertures 32 to mechanically fix the metallic hypotube section 30 to the polymeric shaft 20, as seen in FIG. 5 for example. In some embodiments, the at least one piece of polymeric material 40 may reflow, comingle with, and/or bond with the polymeric shaft 20, thereby forming a monolithic piece of polymer overlapping and extending through the proximal and distal ends of the metallic hypotube section 30, thereby mechanically affixing the metallic hypotube section 30 to the polymeric shaft 20.

Figure 6:
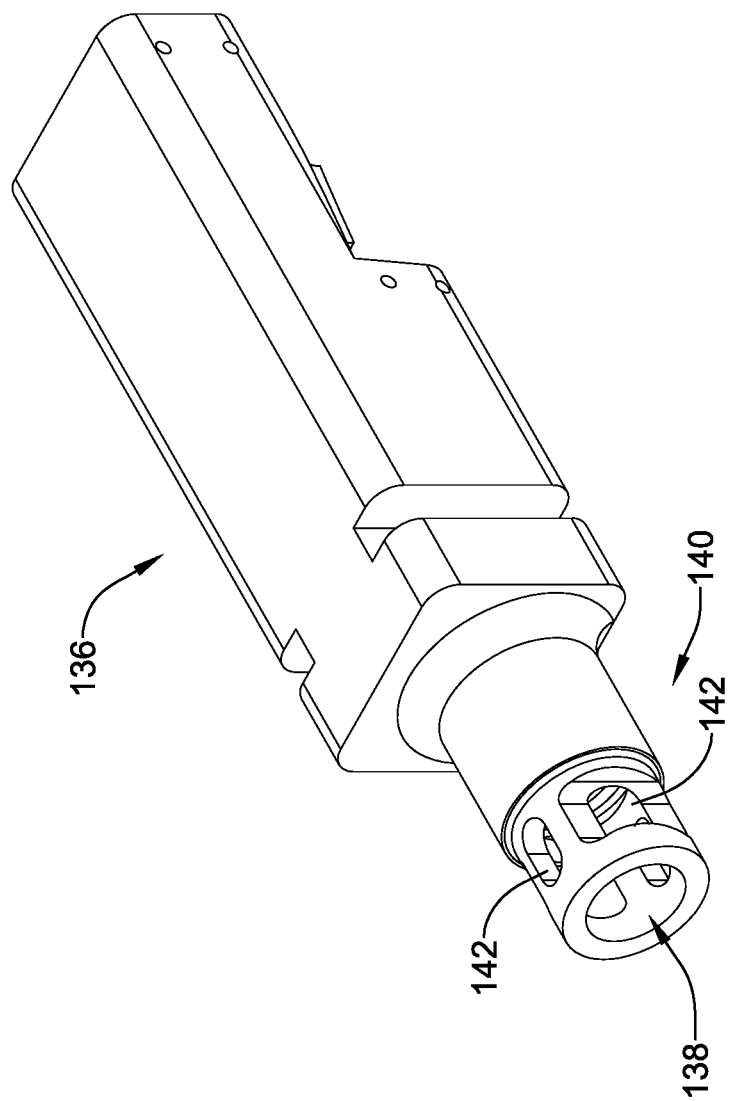
FIG. 6 is a perspective view of an example diverter block of the example medical device system of FIG. 2.
Figure 6A:
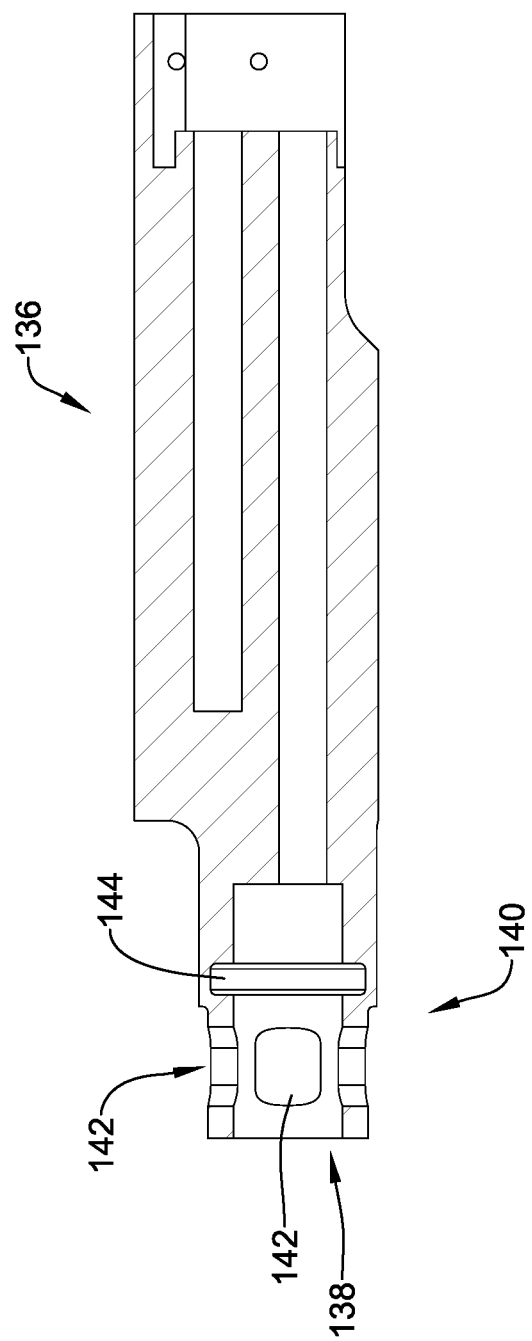
FIG. 6A is a cross-sectional view of the example diverter block of FIG. 6.
Figure 6B:
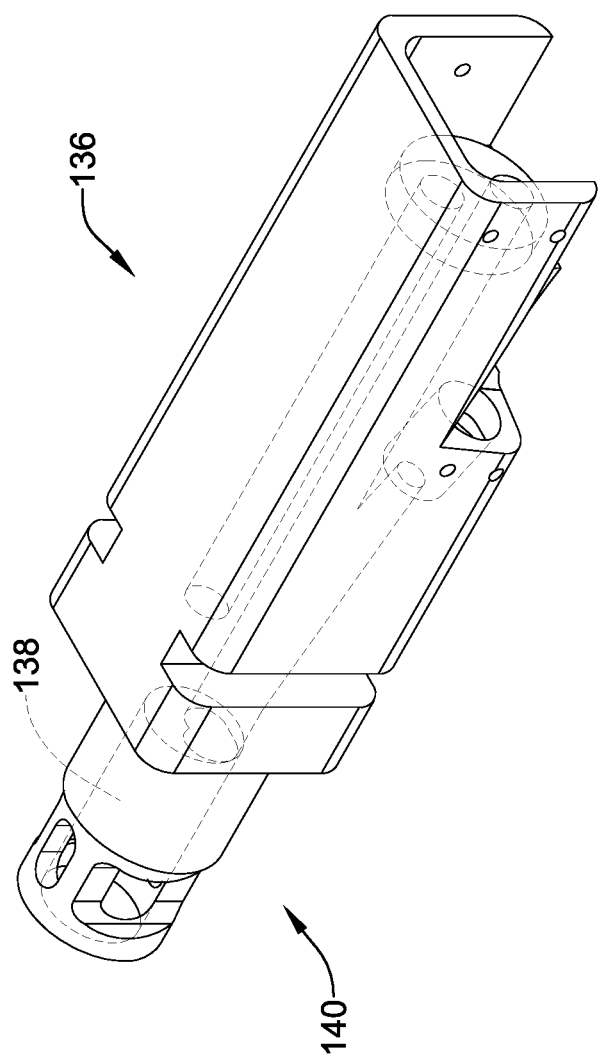
FIG. 6B illustrates selected portions of the example diverter block of FIG. 6.
Figure 7:
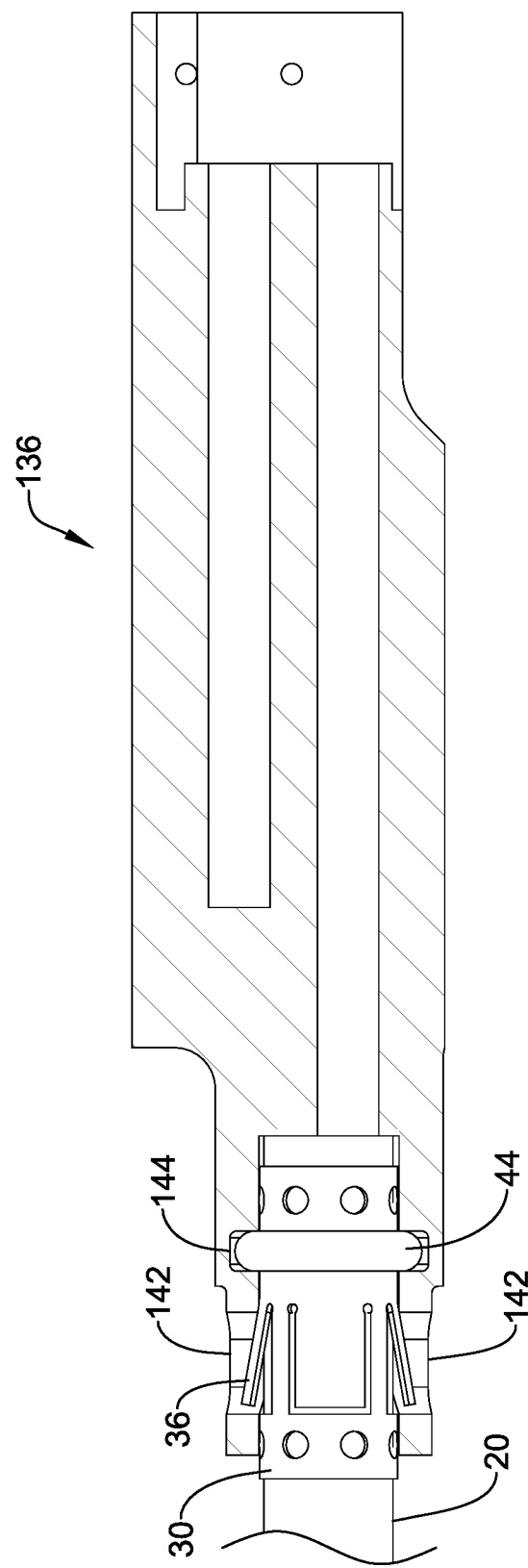
FIG. 7 is a partial cross-sectional view of an example catheter assembly engaged with an example diverter block.

Turning now to FIGS. 6, 6A, and 6B, an example diverter block 136 may include at least one lumen formed therein and/or extending longitudinally therethrough, and a distal mounting portion 140 in fluid communication with the at least one lumen. In some embodiments, the distal mounting portion 140 may be in fluid communication with more than one lumen, as seen in FIG. 6B for example. In some embodiments, the diverter block 136 may be non-movably disposed within an interior cavity of the device handle 18. In some embodiments, the diverter block 136 may be fixedly attached to the device handle 18. In some embodiments, the diverter block 136 may have one or more features that engages one or more corresponding features of the device handle 18, thereby preventing axial, lateral, and/or rotational movement of the diverter block 136 relative to the device handle 18. In some embodiments, the distal mounting portion 140 of the diverter block 136 may include a plurality of windows 142 formed therein. In some embodiments, as will be discussed in more detail below, each prong 36 of the metallic hypotube section 30 of the catheter assembly 14 may engage one of the plurality of windows 142. In some embodiments, the diverter block 136 may include a channel 144 disposed within the distal mounting portion 140, as seen in FIG. 6A. In some embodiments, the channel 144 may be disposed circumferentially about a receiving lumen 138 of the distal mounting portion 140, the receiving lumen 138 being configured to receive and/or engage the proximal portion of the catheter assembly 14 therein, as seen in FIG. 7 for example, as described in more detail below. In some embodiments, the channel 144 may be an annular channel. Other configurations are also contemplated.

In some embodiments, the diverter block 136 may have an equal number of windows 142 to the prongs 36 on the catheter assembly 14. In some embodiments, the diverter block 136 may include more windows 142 than there is prongs 36 on the catheter assembly 14. In at least some embodiments, the plurality of windows 142 may be arranged in complimentary fashion to the prong(s) 36 of the catheter assembly 14 (i.e., common angular displacement, common circumferential distances apart, etc.) such that each prong 36 may be aligned with one of the plurality of windows 142 when the proximal portion of the catheter assembly 14 is inserted into the distal mounting portion 140 of the diverter block 136, as seen in FIG. 7 for example. In some embodiments, the plurality of windows 142 may provide sufficient access to the prong(s) 36 (for example, with a tool or other suitable device) to permit inward pressure to be applied thereto to disengage the prong(s) 36 from the plurality of windows 142 and/or the distal mounting portion 140, so as to permit removal of the catheter assembly 14 from the distal mounting portion 140 and/or disengagement from the diverter block 136.

As illustrated in FIG. 7, in some embodiments, the metallic hypotube section 30 may releasably lock the catheter assembly 14 and/or the polymeric shaft 20 to the diverter block 136 in fluid communication with the at least one lumen of the diverter block 136. When the catheter assembly 14 is locked to the diverter block 136 as described herein, the catheter assembly 14 may be fixed in position relative to the device handle 18. In at least some embodiments, at least a portion of the polymeric shaft 20, when locked to the diverter block 136, may bottom out in the receiving lumen 138, and/or at least a portion of a proximal end of the polymeric shaft 20 may abut a proximal wall or face of the receiving lumen 138, thereby placing one or more of the plurality of lumens of the polymeric shaft 20 in fluid communication with the at least one lumen of the diverter block 136. In some embodiments, a gasket 44 may be disposed on and/or about the smooth portion 38 of the metallic hypotube section 30, and when the catheter assembly 14 is inserted into the distal mounting portion 140, the gasket 44 may be compressed between the smooth portion 38 of the metallic hypotube section 30 and the distal mounting portion 140 of the diverter block 136. In at least some embodiments, the gasket 44 may be inserted into and/or disposed within the channel 144 formed in the distal mounting portion 140.

Figure 8:
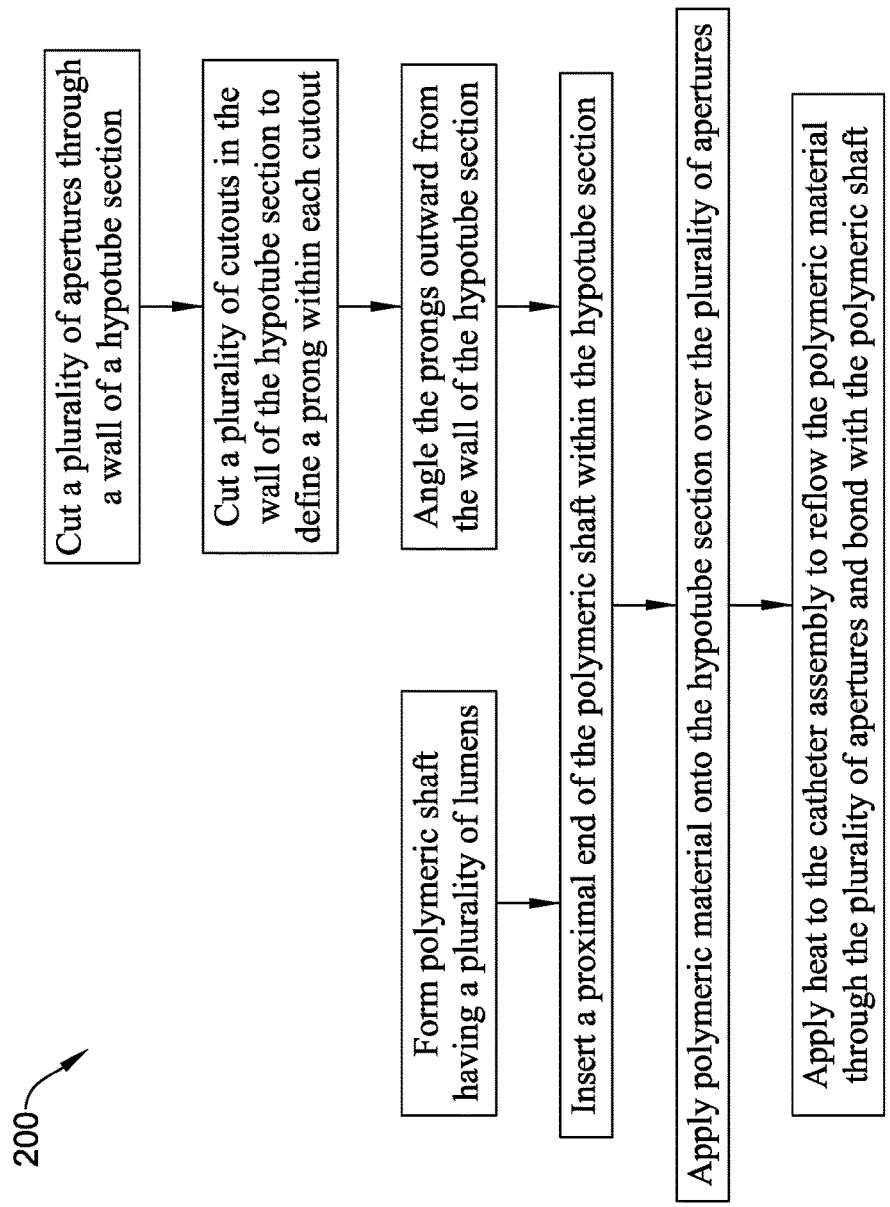
FIG. 8 illustrates an example method of manufacturing of an example catheter assembly.

FIG. 8 illustrates an example method 200 of manufacturing a catheter assembly 14 may include forming a polymeric shaft 20 having a plurality of lumens extending therethrough. In some embodiments, the polymeric shaft 20 may be formed through various extrusion techniques, machining, or other suitable methods. In some embodiments, the method 200 may include cutting a plurality of apertures 32 through a wall of a metallic hypotube section 30. In some embodiments, the plurality of apertures 32 may be cut using a laser, conventional machining, electrical discharge machining, punching, drilling, water jet, or other suitable means. In some embodiments, the method 200 may include cutting a plurality of cutouts 34 in the wall of the metallic hypotube section 30 to define a prong 36 within each cutout 34. In some embodiments, the plurality of cutouts 34 may be cut using a laser, conventional machining, electrical discharge machining, saw cutting, water jet, grinding, punching, or other suitable means. In some embodiments, the method 200 may include angling the prongs 36 radially outward from the wall of the metallic hypotube section 30. In some embodiments, the prongs 36 may be angled radially outward at an oblique angle to the wall of the metallic hypotube section 30. In some embodiments, the plurality of apertures 32 may include a first plurality of apertures and a second plurality of apertures, the first plurality of apertures being disposed proximal of the plurality of cutouts 34 and the second plurality of apertures being disposed distal of the plurality of cutouts 34. In some embodiments, the metallic hypotube section 30 may include a smooth portion 38 configured to engage a gasket 44 surrounding the metallic hypotube section 30, the smooth portion 38 being disposed between the plurality of cutouts 34 and the first plurality of apertures.

In some embodiments, the method 200 may include inserting a proximal end of the polymeric shaft 20 within the metallic hypotube section 30, wherein the prongs 36 extend radially outward from the wall of the metallic hypotube section 30 in the distal direction. In some embodiments, the method 200 may include applying polymeric material 40 onto the metallic hypotube section 30 over the plurality of apertures 32 and/or extending proximal of a proximal end and distal of a distal end of the metallic hypotube section 30. In some embodiments, a first piece of polymeric material 40 may be disposed over the first plurality of apertures and extend proximal of the proximal end of the metallic hypotube section 30, and a second piece of polymeric material 40 may be disposed over the second plurality of apertures and extend distal of the distal end of the metallic hypotube section 30. In some embodiments, the method 200 may include applying heat to the catheter assembly 14 (i.e., to the metallic hypotube section 30 disposed about and/or on the polymeric shaft 20) to reflow the polymeric material 40 through the plurality of apertures and bond with the polymeric shaft 20, thereby mechanically fixing the metallic hypotube section 30 to the polymeric shaft 20.

The materials that can be used for the various components of the medical device system 10 (and/or other systems disclosed herein) and the various tubular members disclosed herein may include those commonly associated with medical devices. For simplicity purposes, the following discussion makes reference to the delivery sheath 12 and/or the catheter assembly 14. However, this is not intended to limit the devices and methods described herein, as the discussion may be applied to other similar tubular members and/or components of tubular members or devices disclosed herein.

The delivery sheath 12, the catheter assembly 14, and/or the metallic hypotube section 30 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of delivery sheath 12 and/or the catheter assembly 14 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MM) compatibility is imparted into the medical device system 10. For example, delivery sheath 12 and catheter assembly 14, or portions thereof, may be made of a material that does not substantially distort the image and create substantial artifacts (i.e., gaps in the image). Certain ferromagnetic materials, for example, may not be suitable because they may create artifacts in an MRI image. Delivery sheath 12 and catheter assembly 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of delivery sheath 12 and catheter assembly 14 that may define a generally smooth outer surface for the medical device system 10. In other embodiments, however, such a sheath or covering may be absent from a portion of all of the medical device system 10, such that delivery sheath 12 and catheter assembly 14 may form an outer surface. The sheath, the delivery sheath 12, the polymeric shaft 20, and/or the diverter block 136 (along with other components of the medical device system 10) may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical device system 10 (including, for example, the exterior surface of delivery sheath 12 and catheter assembly 14) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of delivery sheath 12 and catheter assembly 14, or other portions of the medical device system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A catheter assembly, comprising:
   an elongate polymeric shaft having a plurality of lumens extending therethrough; and
   a metallic hypotube section disposed about and fixedly attached to a proximal end of the polymeric shaft;
   wherein the metallic hypotube section includes a plurality of apertures extending through a wall thereof and a plurality of cutouts each defining a corresponding prong;
   wherein each prong extends radially outward from the wall.

2. The catheter assembly of claim 1, wherein each prong extends radially outward at an oblique angle to the wall.

3. The catheter assembly of claim 1, wherein the metallic hypotube section includes a smooth portion on its outer surface proximal of the plurality of cutouts.

4. The catheter assembly of claim 3, wherein the smooth portion extends uninterruptedly around the metallic hypotube section to form an annular ring.

5. The catheter assembly of claim 3, wherein at least some of the plurality of apertures are disposed proximal of the smooth portion.

6. The catheter assembly of claim 1, wherein at least some of the plurality of apertures are disposed distal of the plurality of cutouts.

7. The catheter assembly of claim 1, further comprising at least one piece of polymeric material disposed about the metallic hypotube section and extending through the plurality of apertures to mechanically fix the metallic hypotube section to the polymeric shaft.

8. A medical device, comprising:
- a device handle having a diverter block non-movably disposed within an interior cavity of the device handle, the diverter block including at least one lumen extending longitudinally therethrough and a distal mounting portion in fluid communication with the at least one lumen;
- a delivery sheath coupled to the device handle; and
- a catheter assembly extending distally from the device handle within the delivery sheath, the catheter assembly comprising:
  - a multi-lumen polymeric shaft coupled to the diverter block; and
  - a metallic hypotube section disposed about and fixedly attached to a proximal end of the polymeric shaft; wherein the metallic hypotube section includes a plurality of apertures extending through a wall thereof and a plurality of cutouts defining a corresponding prong extending radially outward from the wall;
- wherein the metallic hypotube section releasably locks the polymeric shaft to the diverter block in fluid communication with the at least one lumen of the diverter block;
- wherein the delivery sheath is axially translatable relative to the device handle and the catheter assembly is fixed in position relative to the device handle.

9. The medical device of claim 8, wherein the distal mounting portion of the diverter block includes a plurality of windows formed therein, and each prong engages one of the plurality of windows.

10. The medical device of claim 8, wherein each prong extends radially outward at an oblique angle to the wall.

11. The medical device of claim 8, wherein the hypotube section includes a smooth portion on its outer surface proximal of the plurality of cutouts.

12. The medical device of claim 11, further including a gasket compressed between the smooth portion of the metallic hypotube section and the distal mounting portion of the diverter block.

13. The medical device of claim 12, wherein the gasket is disposed within a channel formed in the distal mounting portion.

14. The medical device of claim 8, wherein the catheter assembly further comprises at least one piece of polymeric material disposed about the metallic hypotube section and extending through the plurality of apertures to mechanically fix the metallic hypotube section to the polymeric shaft.

15. A method of manufacturing a catheter assembly, comprising:
- forming a polymeric shaft having a plurality of lumens extending therethrough;
- cutting a plurality of apertures through a wall of a hypotube section;
- cutting a plurality of cutouts in the wall of the hypotube section to define a prong within each cutout;
- angling the prongs radially outward from the wall of the hypotube section;
- inserting a proximal end of the polymeric shaft within the hypotube section;
- applying polymeric material onto the hypotube section over the plurality of apertures; and
- applying heat to the catheter assembly to reflow the polymeric material through the plurality of apertures and bond with the polymeric shaft, thereby mechanically fixing the hypotube section to the polymeric shaft.

16. The method of claim 15, wherein the plurality of cutouts is cut using a laser.

17. The method of claim 15, wherein the plurality of apertures is cut using a laser.

18. The method of claim 15, wherein the prongs are angled radially outward at an oblique angle to the wall of the hypotube section.

19. The method of claim 15, wherein the plurality of apertures includes a first plurality of apertures and a second plurality of apertures, the first plurality of apertures being disposed proximal of the plurality of cutouts and the second plurality of apertures being disposed distal of the plurality of cutouts;
wherein the hypotube section includes a smooth portion configured to engage a gasket surrounding the hypotube section, the smooth portion being disposed between the plurality of cutouts and the first plurality of apertures.

* * * * *